US007776338B2

(12) United States Patent
Connell et al.

(10) Patent No.: US 7,776,338 B2
(45) Date of Patent: *Aug. 17, 2010

(54) ADJUVANT ACTIVITIES OF MUTANTS OF LT-IIA AND LT-IIB ENTEROTOXIN LACKING BINDING TO GANGLIOSIDE

(75) Inventors: Terry D. Connell, Williamsville, NY (US); Michael W. Russell, East Amherst, NY (US); Hesham Nawar, Buffalo, NY (US); Sergio Arce, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/265,516

(22) Filed: Nov. 5, 2008

(65) Prior Publication Data

US 2009/0136535 A1 May 28, 2009

Related U.S. Application Data

(62) Division of application No. 10/950,822, filed on Sep. 27, 2004, now Pat. No. 7,455,843.

(60) Provisional application No. 60/505,961, filed on Sep. 25, 2003.

(51) Int. Cl.

| | |
|---|---|
| ***A61K 39/02*** | (2006.01) |
| ***A61K 39/00*** | (2006.01) |
| ***A61K 39/385*** | (2006.01) |
| ***A61K 39/108*** | (2006.01) |
| ***A61K 45/00*** | (2006.01) |
| ***A61K 39/116*** | (2006.01) |
| ***A01N 37/18*** | (2006.01) |

(52) U.S. Cl. ............. 424/190.1; 424/192.1; 424/184.1; 424/193.1; 424/234.1; 424/236.1; 424/257.1; 424/282.1; 424/203.1; 514/2

(58) Field of Classification Search ...................... None
See application file for complete search history.

(56) References Cited

U.S. PATENT DOCUMENTS

| | | | | |
|---|---|---|---|---|
| 7,455,843 | B2 * | 11/2008 | Connell et al. ........... | 424/236.1 |
| 2002/0004238 | A1 | 1/2002 | Russell et al. | |

FOREIGN PATENT DOCUMENTS

| | | | |
|---|---|---|---|
| WO | 0127144 | A2 | 4/2001 |

OTHER PUBLICATIONS

Connell et al.; Molecular Genetic Analysis of Ganglioside GD1b-Binding Activity of *Escherichia coli* Type IIa Heat-Labile Enterotoxin by Use of Random and Site-Directed Mutagenesis; Infection and Immunity, Jan. 1992, vol. 60, No. 1; pp. 63-70.

Connell et al.; Mutational analysis of the ganglioside-binding activity of the type II *Escherichia coli* heat-labile enterotoxin LT-IIb; Molecular Microbiology, 1995, vol. 16, No. 1; pp. 21-31.

Pickett et al.; Genetics of type IIa Heat-Labile Enterotoxin of *Escherichia coli*: Operon Fusions, Nucleotide Sequence, and Hybridization Studies; Journal of Bacteriology, Nov. 1987, vol. 169, No. 11; pp. 5180-5187.

Nawar et al.; Mucosal Adjuvant Properties of Mutant LT-IIa and LT-IIb Enterotoxins That Exhibit Altered Ganglioside-Binding Activities; Infection and Immunity, Mar. 2005, vol. 73, No. 3; pp. 1330-1342.

Connell et al.; Characterization of Hybrid Toxins Produced in *Escherichi coli* Assembly of A and B Polypeptides from Type I and Type II Heat-Labile Enterotoxins; Infection and Immunity, Apr. 1992, vol. 60; pp. 1653-1661.

Martin et al.; Recombinant Antigen-Enterotoxin A2/B Chimeric Mucosal Immunogens Differentially Enhance Antibody Responses and B7-Dependent Costimulation of CD4+ T Cells; Infection and Immunity, Jan. 2001, vol. 69, No. 1; pp. 252-261.

Martin et al.; Distinct Cytokine Regulation by Cholera Toxin and Type II Heat-Labile Toxins Involves Differential Regulation of CD40 Ligand on CD4+ T Cells; Infection and Immunity, Jul. 2001, vol. 69, No. 7; pp. 4486-4492.

Martin et al.; Comparative Analysis of the Mucosal Adjuvanticity of the Type II Heat-Labile Enterotoxins LT-IIa and LT-IIb; Infection and Immunity, Jan. 2000, vol. 68, No. 1; pp. 281-287.

Connell et al.; Immunostimulatory activity of LT-IIa, a type II heat-labile enterotoxin of *Escherichia coli*; Elsevier Immunology Letters 62 (1998); pp. 117-120.

Martin et al.; Immunomodulatory Effects of Type I and Type II Heat-Labile Enterotoxins on Mucosal and Systemic Immunity; Dissertation, 2000, Birmingham, Alabama; 152 pages.

* cited by examiner

*Primary Examiner*—S. Devi
(74) *Attorney, Agent, or Firm*—Hodgson Russ LLP

(57) ABSTRACT

The present invention describes the adjuvant activity of mutants of LT-IIa and LT-IIb enterotoxin which lack ganglioside binding activity. The adjuvant activity of the LT-IIb (T13I) mutant is comparable to that of the wild type LT-IIb. The adjuvant activity of LT-IIa(T34I) mutant is also described which exhibits a late onset adjuvant activity. These mutants are useful for enhancing immune response to antigens.

8 Claims, 7 Drawing Sheets

SEQUENCE LISTING

```
<160> NUMBER OF SEQ ID NOS: 6

<210> SEQ ID NO 1
<211> LENGTH: 123
<212> TYPE: PRT
<213> ORGANISM: Escherichia coli
<220> FEATURE:
<223> OTHER INFORMATION: LT-IIa B polypeptide

<400> SEQUENCE: 1

Met Ser Ser Lys Lys Ile Ile Gly Ala Phe Val Leu Met Thr Gly
                5                   10                  15

Ile Leu Ser Gly Gln Val Tyr Ala Gly Val Ser Glu His Phe Arg
                20                  25                  30

Asn Ile Cys Asn Gln Thr Thr Ala Asp Ile Val Ala Gly Val Gln
                35                  40                  45

Leu Lys Lys Tyr Ile Ala Asp Val Asn Thr Asn Thr Arg Gly Ile
                50                  55                  60

Tyr Val Val Ser Asn Thr Gly Gly Val Trp Tyr Ile Pro Gly Gly
                65                  70                  75

Arg Asp Tyr Pro Asp Asn Phe Leu Ser Gly Glu Ile Arg Lys Thr
                80                  85                  90

Ala Met Ala Ala Ile Leu Ser Asp Thr Lys Val Asn Leu Cys Ala
                95                  100                 105
```

-continued

```
Lys Thr Ser Ser Ser Pro Asn His Ile Trp Ala Met Glu Leu Asp
                110                 115                 120

Arg Glu Ser


<210> SEQ ID NO 2
<211> LENGTH: 100
<212> TYPE: PRT
<213> ORGANISM: Escherichia coli
<220> FEATURE:
<223> OTHER INFORMATION: LT-IIa B mature polypeptide

<400> SEQUENCE: 2

Gly Val Ser Glu His Phe Arg Asn Ile Cys Asn Gln Thr Thr Ala
                5                   10                  15

Asp Ile Val Ala Gly Val Gln Leu Lys Lys Tyr Ile Ala Asp Val
                20                  25                  30

Asn Thr Asn Thr Arg Gly Ile Tyr Val Val Ser Asn Thr Gly Gly
                35                  40                  45

Val Trp Tyr Ile Pro Gly Gly Arg Asp Tyr Pro Asp Asn Phe Leu
                50                  55                  60

Ser Gly Glu Ile Arg Lys Thr Ala Met Ala Ala Ile Leu Ser Asp
                65                  70                  75

Thr Lys Val Asn Leu Cys Ala Lys Thr Ser Ser Ser Pro Asn His
                80                  85                  90

Ile Trp Ala Met Glu Leu Asp Arg Glu Ser
                95                  100


<210> SEQ ID NO 3
<211> LENGTH: 100
<212> TYPE: PRT
<213> ORGANISM: Escherichia coli
<220> FEATURE:
<223> OTHER INFORMATION: LT-IIa(T34I)mutant

<400> SEQUENCE: 3

Gly Val Ser Glu His Phe Arg Asn Ile Cys Asn Gln Thr Thr Ala
                5                   10                  15

Asp Ile Val Ala Gly Val Gln Leu Lys Lys Tyr Ile Ala Asp Val
                20                  25                  30

Asn Thr Asn Ile Arg Gly Ile Tyr Val Val Ser Asn Thr Gly Gly
                35                  40                  45

Val Trp Tyr Ile Pro Gly Gly Arg Asp Tyr Pro Asp Asn Phe Leu
                50                  55                  60

Ser Gly Glu Ile Arg Lys Thr Ala Met Ala Ala Ile Leu Ser Asp
                65                  70                  75

Thr Lys Val Asn Leu Cys Ala Lys Thr Ser Ser Ser Pro Asn His
                80                  85                  90

Ile Trp Ala Met Glu Leu Asp Arg Glu Ser
                95                  100


<210> SEQ ID NO 4
<211> LENGTH: 122
<212> TYPE: PRT
<213> ORGANISM: Escherichia coli
<220> FEATURE:
<223> OTHER INFORMATION: LT-IIb B polypeptide
```

-continued

<400> SEQUENCE: 4

```
Met Ser Phe Lys Lys Ile Ile Lys Ala Phe Val Ile Met Ala Ala
                5                   10                  15

Leu Val Ser Val Gln Ala His Ala Gly Ala Ser Gln Phe Phe Lys
                20                  25                  30

Asp Asn Cys Asn Arg Thr Thr Ala Ser Leu Val Glu Gly Val Glu
                35                  40                  45

Leu Thr Lys Tyr Ile Ser Asp Ile Asn Asn Asn Thr Asp Gly Met
                50                  55                  60

Tyr Val Val Ser Ser Thr Gly Gly Val Trp Arg Ile Ser Arg Ala
                65                  70                  75

Lys Asp Tyr Pro Asp Asn Val Met Thr Ala Glu Met Arg Lys Ile
                80                  85                  90

Ala Met Ala Ala Val Leu Ser Gly Met Arg Val Asn Met Cys Ala
                95                  100                 105

Ser Pro Ala Ser Ser Pro Asn Val Ile Trp Ala Ile Glu Leu Glu
                110                 115                 120

Ala Glu
```

<210> SEQ ID NO 5
<211> LENGTH: 99
<212> TYPE: PRT
<213> ORGANISM: Escherichia coli
<220> FEATURE:
<223> OTHER INFORMATION: LT-IIb B mature polypeptide

<400> SEQUENCE: 5

```
Gly Ala Ser Gln Phe Phe Lys Asp Asn Cys Asn Arg Thr Thr Ala
                5                   10                  15

Ser Leu Val Glu Gly Val Glu Leu Thr Lys Tyr Ile Ser Asp Ile
                20                  25                  30

Asn Asn Asn Thr Asp Gly Met Tyr Val Val Ser Ser Thr Gly Gly
                35                  40                  45

Val Trp Arg Ile Ser Arg Ala Lys Asp Tyr Pro Asp Asn Val Met
                50                  55                  60

Thr Ala Glu Met Arg Lys Ile Ala Met Ala Ala Val Leu Ser Gly
                65                  70                  75

Met Arg Val Asn Met Cys Ala Ser Pro Ala Ser Ser Pro Asn Val
                80                  85                  90

Ile Trp Ala Ile Glu Leu Glu Ala Glu
                95
```

<210> SEQ ID NO 6
<211> LENGTH: 99
<212> TYPE: PRT
<213> ORGANISM: Escherichia coli
<220> FEATURE:
<223> OTHER INFORMATION: LT-IIb(T13I) mutant

<400> SEQUENCE: 6

```
Gly Ala Ser Gln Phe Phe Lys Asp Asn Cys Asn Arg Ile Thr Ala
                5                   10                  15

Ser Leu Val Glu Gly Val Glu Leu Thr Lys Tyr Ile Ser Asp Ile
                20                  25                  30

Asn Asn Asn Thr Asp Gly Met Tyr Val Val Ser Ser Thr Gly Gly
                35                  40                  45
```

-continued

```
Val Trp Arg Ile Ser Arg Ala Lys Asp Tyr Pro Asp Asn Val Met
                50                  55                  60

Thr Ala Glu Met Arg Lys Ile Ala Met Ala Ala Val Leu Ser Gly
                65                  70                  75

Met Arg Val Asn Met Cys Ala Ser Pro Ala Ser Ser Pro Asn Val
                80                  85                  90

Ile Trp Ala Ile Glu Leu Glu Ala Glu
                95
```

ADJUVANT ACTIVITIES OF MUTANTS OF LT-IIA AND LT-IIB ENTEROTOXIN LACKING BINDING TO GANGLIOSIDE

This application is a divisional application of U.S. application Ser. No. 10/950,822, filed Sep. 27, 2004, now U.S. Pat. No. 7,455,843, which claims priority to U.S. provisional application No. 60/505,961, filed on Sep. 25, 2003, the disclosures of which are incorporated herein by reference.

This work was supported by funding from the National Institutes of Health Grant no. DE 13833. The Government has certain rights in the invention.

FIELD OF THE INVENTION

The present invention relates generally to the field of adjuvants and more particularly provides mutant enterotoxins which can be used as adjuvants.

DISCUSSION OF RELATED ART

Published observations demonstrate that several heat-labile enterotoxins (cholera toxin of *Vibrio cholerae* and the LT-I, LT-IIa, and LT-IIb enterotoxins of *Escherichia coli*) each exhibit adjuvant activity in murine models when co-administered either systemically or mucosally with an antigen. Each of these adjuvants stimulate distinctive and disparate patterns of immune responsiveness (antibody subclass, cytokine expression, co-stimulatory ligand expression, etc.) to that antigen. It is generally held that the adjuvant activities of the enterotoxins depend upon their binding to different ganglioside receptors found on the surface of eukaryotic cells. CT and LT-I bind to GM1; LT-IIa binds with decreasing affinity to GD1b, GD1a, and GM1; LT-IIb binds to GD1a. It is believed that binding of these gangliosides by the enterotoxins initiates one or more signal transduction cascades which are responsible for eliciting the various immune responses mentioned above.

There is great interest in developing vaccines that can be administered by needle-free methods, for example, orally or intranasally. Besides ease of administration and the avoidance of costs and hazards associated with needles, these have numerous advantages in the induction of responses at mucosal surfaces such as the gastrointestinal, respiratory, and genital tracts, which are not effectively protected by conventional immunization by injection. Progress has been hampered by the lack of safe and effective vaccine adjuvants applicable to these mucosal routes of immunization. Although enterotoxins such as cholera toxin, LT-I, LT-IIa, and LT-IIb, are very effective in experimental animals, they are currently considered to be toxic for humans. We and others, however, have shown that in some instances, their nontoxic B subunits may be effective adjuvants by the intranasal route for the induction of antibodies in blood, saliva, respiratory, and genital secretions. Recent concern, nevertheless, has focused on the potential of either the intact enterotoxins or their respective B subunits to bind olfactory nerves in the nose and to be trafficked to the brain. While the pathological affects of such transfer has not been confirmed, it is possible that enterotoxin delivery to the brain could have pathological side-effects. These side-effects would likely preclude the use of these molecules in humans as intranasal adjuvants. Binding and trafficking of the enterotoxins via the olfactory nerve is believed to depend upon binding of the enterotoxins and B subunits to ganglioside receptors which are abundant in nerve tissue.

Thus, in the field of vaccine development, there is an huge but unmet need for safe and effective vaccine adjuvants applicable to mucosal immunization in humans. While heat-labile enterotoxins and their derivatives have been shown in numerous laboratories to be among the most effective mucosal adjuvants in experimental animal models, their applicability to humans is precluded by the toxicity of the intact holotoxins and by the olfactory nerve uptake of either the holotoxins or their respective B subunits.

SUMMARY OF THE INVENTION

Recombinant LT-IIa and LT-IIb enterotoxins in which the threonine at amino acid position 34 for LT-IIa (referred to herein as LT-IIa(T34I)) and at position 13 for LT-IIb in the B polypeptide has been substituted with isoleucine (referred to herein as LT-IIb(T13I)) were tested for adjuvant activities. The LT-IIa(T34I) mutant has been shown previously to lack binding to gangliosides GD1b, GD1b, and GD1a, while the LT-IIb(T13I) mutant has been shown to lack binding to ganglioside GD1b, the only ganglioside bound by wt LT-IIb (Connell et al., 1992. Infect. Immun., 60:63-70; Connell et al., Mol. Microbiol., 16:21-31).

In the present invention it was unexpectedly observed that the mutant LT-IIa(T13I) and LT-IIb (T13I) enhanced immune response. The mutant LT-IIb(T13I) was found to exhibit a strong initial immune response as well as a delayed "memory" response. Its adjuvant activity was equivalent to that of the wild type enterotoxin in a murine intranasal immunization model. In the same model, no augmented antibody response for the LT-IIa(T34I) mutant was observed at time points close to the initial immunizations. However, this mutant primed the animal to respond to a later administered antigen and therefore, immunization with LT-IIa(T34I) may prime the animal for a "memory" response.

With respect to LT-IIb(T13I), flow cytometry has demonstrated that the mutant toxin fails to bind to: CD4+ T-cells, CD8+ T-cells, B-cells macrophages, or dendritic cells from either spleen or cervical lymph nodes. In contrast, wild type LT-IIb binds to most, if not all of these lymphoid cell types, to one degree or another. Since the mutant LT-IIb(T13I) lacks detectable ganglioside binding activity, and since ganglioside binding is considered to be associated with retrograde trafficking of the enterotoxin molecules from olfactory nerve to brain, the mutant of the present invention can potentially be used as an adjuvant without the side-effects associated with retrograde trafficking. Further, these mutants have been shown to lack toxic activity in an in vitro mouse Y1 adrenal cell assay, a sensitive assay for measuring enterotoxicity of heat-labile enterotoxins.

Thus, mutants of LT-IIa and LT-IIb which lack ganglioside binding activity can be used as adjuvants. In one embodiment, a method is provided to enhance immunogenic response to an antigen by administering an adjuvant selected from the group consisting of mutants with amino acid substitutions at 13 position for LT-IIb(T13I) and at position 34 for LT-IIa(T34I).

DETAILED DESCRIPTION OF THE INVENTION

Figure 1:
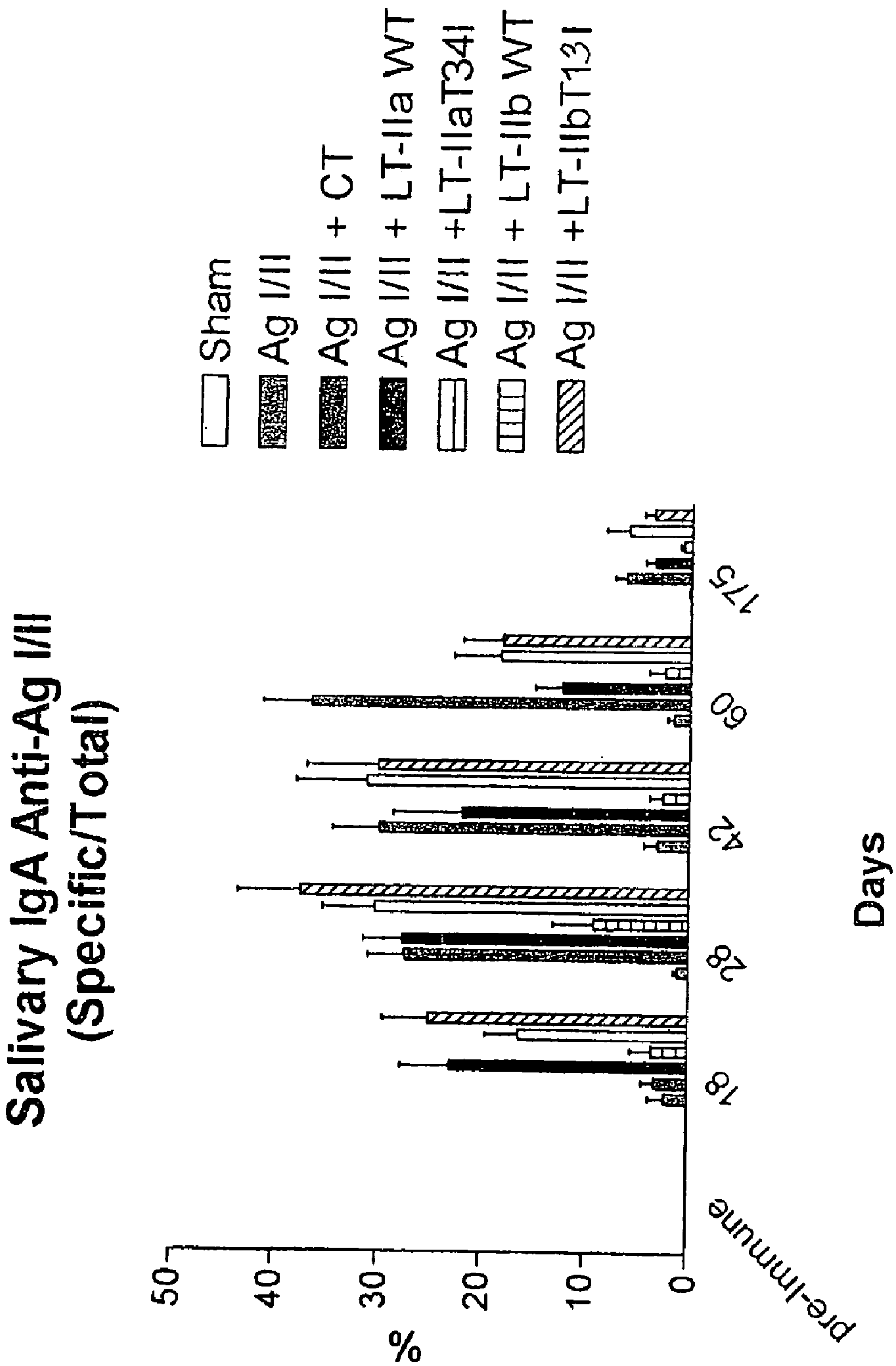
FIG. 1 is a representation of salivary IgA anti-Ag I/II levels with our without CT, wild type (WT) LT-IIa, LT-IIa—T34 I mutant, LT-IIb WT, and LT-IIb T-13I mutant. Data are shown at before immunization, and 18, 28, 42, 60 and 175 days after immunization.

The present invention is based on the unexpected finding that mutants of LT-IIa and LT-IIb which lack ganglioside binding activity retain adjuvant activity. Accordingly, the present invention provides a method for enhancing the immune response comprising the steps of administering an antigen with mutants of LT-IIa that do not bind to GD1a, GD1b and GM1 but retain adjuvant activity and/or mutants of LT-IIb which lack ganglioside binding activity to GD1a but retain adjuvant activity.

LT-IIb is an oligomeric protein composed of one A polypeptide and five B polypeptides. While the A polypeptide harbors the "toxic" activity of the molecules, the B polypeptides, which are arranged into a pentamer, exhibit the GD1a ganglioside-binding activity. A mutant was engineered in which the threonine at amino acid position 13 of the B polypeptide was substituted for isoleucine. This mutant has been shown previously by ganglioside-dependent ELISA to have lost all detectible binding to the ganglioside. This recombinant mutant LT-IIb was purified by chromatography and compared with wild type LT-IIb in a murine mucosal model for adjuvant activity. In all cases (serum IgG, serum IgA, vaginal IgA, and salivary IgA), the immune response induced by the mutant was identical to that induced by the wild type enterotoxin.

LT-IIa binds specifically, in descending order of avidity, to gangliosides GD1b, GM1, GT1b, GQ1b, GD2, GD1a and GM3. Substitution of threonine by isoleucine at amino acid position 34 of LT-IIa and substitution of threonine by isoleucine at position 13 of LT-IIb abolishes binding activity of the enterotoxins for their specific ganglioside receptors (Connell et al., 1992. Infect. Immun., 60:63-70; Connell et al., 1995, Mol. Microbiol., 16:21-31). While no augmented antibody response for the LT-IIa(T34I) mutant was observed at time points close to the initial immunizations, this mutant primed the animal to respond to a later administered antigen. Therefore, immunization with LT-IIa(T34I) may prime the animal for a "memory" response. Accordingly, it can be useful as a mucosal and systemic adjuvant.

Flow cytometry experiments on lymphoid cells taken from spleen and cervical lymph nodes showed that the mutant toxin failed to bind to T-cells, B-cells, dendritic cells or macrophages. The mutant, however, did bind to a minor and unidentified cell type from those lymphoid tissues.

The sequence of the wild type LT-IIa B polypeptide is as follows:

(SEQ ID NO: 1)

```
MSSKKIIGAFVLMTGILSGQVYAGVSEHFRNICNQTTADIVAG
VQLKKYIADVNTNTRGIYVVSNTGGVWYIPGGRDYPDNFLSGEIRKTAM
AAILSDTKVNLCAKTSSSPNHIWAMELDRES
```

The first 23 amino acids represent the leader sequence and the sequence of the mature polypeptide is as follows.

(SEQ ID NO: 2)

```
GVSEHFRNICNQTTADIVAGVQLKKYIADVNTNTRGIYVVSNTGG
VWYIPGGRDYPDNFLSGEIRKTAMAAILSDTKVNLCAKTSSSPNHIWAME
LDRES.
```

The sequence of the wt LT-IIb B polypeptide is (SEQ ID NO: 4)

```
MSFKKIIKAFVIMAALVSVQAHAGASQFFKDNCNRTTASLVEG
VELTKYISDINNNTDGMYVVSSTGGVWRISRAKDYPDNVMTAEMRKIAMA
AVLSGMRVNMCASPASSPNVIWAIELEAE.
```

The first 23 amino acids represent the leader sequence and the sequence of the mature polypeptide is as follows:

(SEQ ID NO: 5)

```
GASQFFKDNCNRTTASLVEGVELTKYISDINNNTDGMYVVSSTG
GVWRISRAKDYPDNVMTAEMRKIAMAAVLSGMRVNMCASPASSPNVIWAI
ELEAE
```

The amino acid sequence of LT-IIb(T13I) polypeptide has the sequence shown as SEQ ID NO: 6. The complete sequence of LT-IIb and the demonstration that this mutant is non-toxic is available in Connell et al., 1995, Molecular Microbiology, 16:21-31, incorporated herein by reference.

The amino acid sequence of the LT-IIa(T34I) mutant is shown as SEQ ID NO:3. The complete sequence of the LT-IIa polypeptide is available as Accession no. M17894 and the complete sequence of the LT-IIb polypeptide is available as Accession no. M28523.

The present invention provides a method of inducing or increasing antigen-specific immune response in an individual by co-administration of the antigen and the mutant of LT-IIb as described herein.

In one embodiment of the present invention, the antigen and the adjuvant are administered to an individual using standard methods. They can be co-administered or administered separately. Administration may be mucosal (e.g., intranasal, ocular, gastrointestinal, oral, rectal and genitourinary tract) or parenteral (e.g., intraperitoneal, intravenous, subcutaneous or intramuscular.). Individuals that may be treated using the method of the invention include, but are not limited to humans, cows, horses, pigs, dogs, cats, sheep goats, rabbits, rats, mice and birds. The immune response may be systemic or mucosal.

In one embodiment of the present invention, the antigen is AgI/II. However, those skilled in the art will recognize that this method can be used to increase the immune response to any antigen. Thus, this method can be used for cancer vaccines, viral vaccines, bacterial vaccines or parasitic vaccines or in vaccines to induce tolerance to antigens for treatment of allergies and autoimmune diseases.

In addition to being used as a co-mingled adjuvant, enterotoxins especially their B subunits can be used as carriers of antigens coupled to them to increase the immune response to the coupled antigen. This is particularly advantageous for mucosal routes of immunization to enhance the delivery of the antigen to the immune response tissues. Examples of antigens that may be coupled in this way include proteins, segments of proteins, polypeptides, peptides, and carbohydrates. Antigens can be coupled to enterotoxin B subunits in different ways. Proteins, polypeptides, peptides, or carbohydrates can be chemically conjugated to enterotoxin B subunits by means of various well-known coupling agents and procedures, for example: glutaraldehyde, carbodiimide, bis-diazotized benzidine, maleimidobenzoyl-N-hydroxysuccinimide ester, N-succinimidyl-(3-[2-pyridyl]-dithio) propionate, cyanogen bromide, and periodate oxidation followed by Schiff base formation. Peptides or polypeptides can also be genetically fused to the N-terminus or C-terminus, or inserted into exposed loops of enterotoxin B subunits by recombinant genetic engineering technology. Further, proteins, polypeptides, or peptides can be fused to the A2 subunit of enterotoxins and co-expressed with B subunits of enterotoxins to create recombinant chimeric proteins of the form: Ag-A2/B, in which the toxic A1 subunit of the enterotoxin is replaced by the antigen of choice. The ability of the mutant LT-IIb to stimulate mucosal and systemic immune responses against co-administered vaccine antigens in the absence of binding to gangliosides is advantageous, as it offers the potential to develop a safe and effective mucosal (intranasal or oral) adjuvant for human use. Immune stimulation by this mutant enterotoxin should avoid problems of neural uptake and transmission to the brain, as well as enterotoxicity, which have precluded the use of other enterotoxin-based adjuvants in human vaccines.

The present disclosure provides data for the use of a non-ganglioside-binding mutants of LT-IIa and LT-IIb as a mucosal vaccine adjuvants when co-administered with an appropriate antigen. From the teachings of the disclosure presented herein, several application, including the following, can be developed by those skilled in the art.

1. the adjuvant activities and cell-binding patterns of other non-ganglioside-binding mutants of this or other enterotoxins. Such mutants include, for LT-IIa (Connell et al., Infection and Immunity, 60:63-70, 1992), substitutions of I, P, G, N, L, R for T at the $13^{th}$ position; substitutions of I, P, D, H, N for T at the $14^{th}$ position; substitutions of I, A, G, M, H, L, R, Q for T at the $34^{th}$ position; and for LT-IIb (Connell et al., Molecular Microbiology 16:21-31, 1995), substitutions of I, K, N for T at the $13^{th}$ position; and substitutions of I, N, R, M, K for T at the $14^{th}$ position.

A non-limiting example of such mutants is LT-IIb(T141), LT-IIa(T13I), (T14I). It will also be recognized by those skilled in the art that similar mutants of LT-I which lack binding to GM1 but retain adjuvant activity can be used for the present invention.

2. Use of these and other mutants of the B subunits with altered ganglioside-binding activities as co-administered adjuvants;

3. Use of these and other B subunit mutants with altered ganglioside-binding activities when coupled to vaccine antigens in the form of: chemically conjugated antigen/mutant B subunit molecules; genetic fusions of antigens to mutant B subunit; and recombinant antigen-A2/mutant B subunit chimeric protein for use as mucosal antigen delivery systems (Martin et al., Infect. Immun. 69:252:261; for constructing recombinant chimeric antigen-CTA2/B (U.S. Pat. No. 6,030, 624; J. Immunol., 1995, 154:4332) or antigen-(LT-11)A2/B chimeric proteins, but now mutants B polypeptides with altered ganglioside-binding activities to avoid problems associated with olfactory nerve uptake.

Accordingly, in one embodiment, the present invention also provides mutants of LT-IIa and LT-IIb which lack ganglioside binding activity but retain the adjuvant activity. These mutants can be used as individual molecules or chemically conjugated to the antigen, fused to the antigen or as part of a chimeric enterotoxin molecule in which the B subunit comprises the mutant molecule.

EXAMPLE 1

This example describes evaluating the adjuvant activity of the mutant of the present invention. To determine the effect of the mutant Type II enterotoxins on immunomodulation, female BALB/c mice were immunized intranasally with *S. mutans* AgI/II without or with cholera toxin (CT), wild type (wt) LT-IIa, wt LT-IIb, T341 mutant of LT-IIa or T131 mutant of LT-IIb as follows. Groups of 8 mice were immunized three times at 10-day intervals with AgI/II (10 μg) alone or with AgI/II in combination with 1 μg of CT, LT-IIa, LT-IIa(T34I), LT-IIb, or LT-IIb(T13I). Immunizations were administered in a standardized volume of 10 μl, applied slowly to both external nares. At day 203 after initial immunization all groups were re-immunized with 5 μg of AgI/II alone. The magnitude of the systemic and mucosal immune responses to AgI/II and to the enterotoxins were measured in saliva, serum, and vaginal washes one day before the initial immunization and at 18, 28, 42, and 60 days. Samples were analyzed for IgA and IgG using and the appropriate anti-mouse Ig isotype specific antibody.

Figure 4:
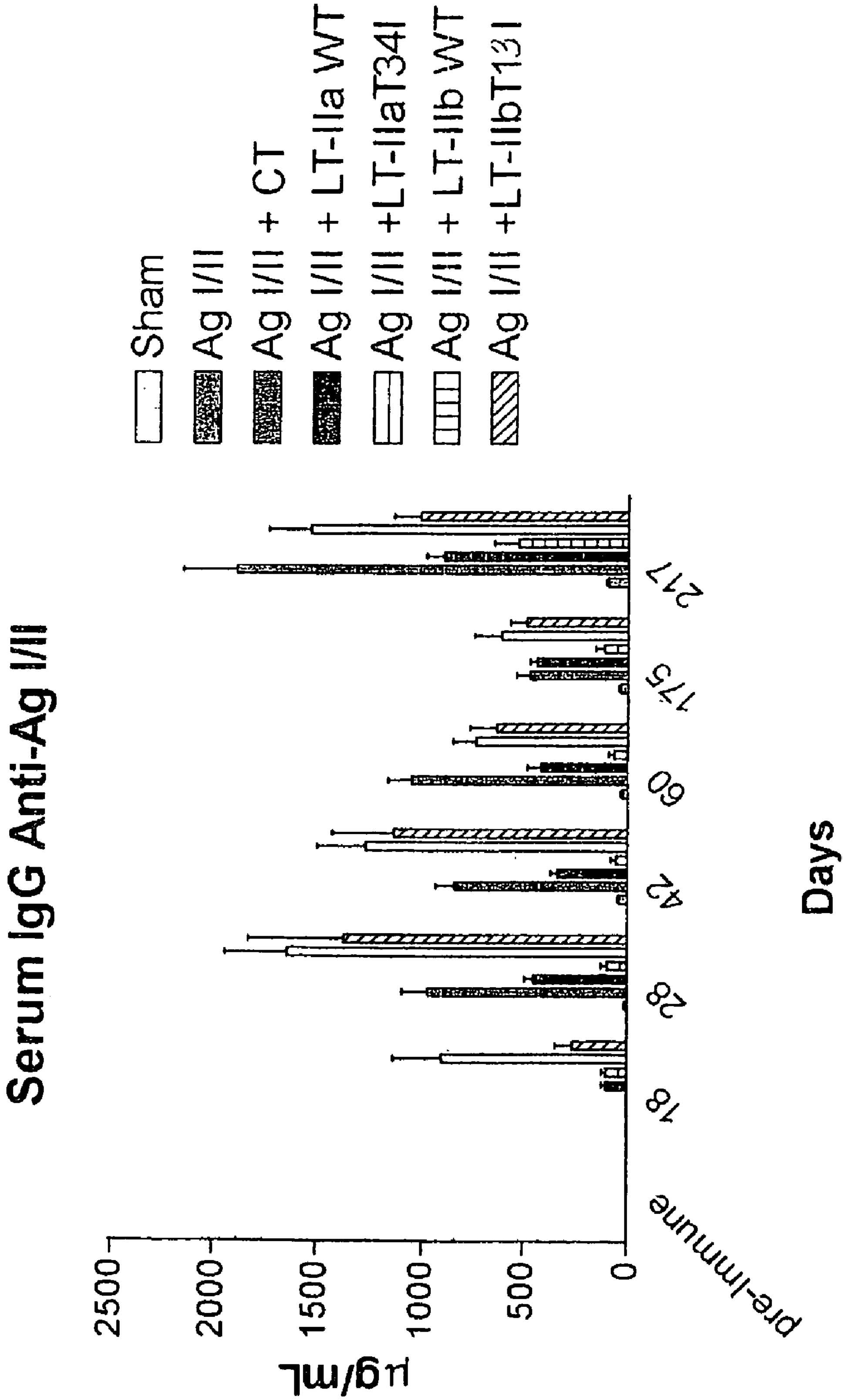
FIG. 4 is a representation of serum IgG anti-Ag I/II levels with our without CT, wild type (WT) LT-IIa, LT-IIa—T34 I mutant, LT-IIb WT, and LT-IIb T-131 mutant. Data are shown at before immunization, and 18, 28, 42, 60, 175 and 217 days after immunization.

The results are shown in FIGS. 1-4. As shown in FIG. 1, after 18 days, salivary IgA responses to AgI/II were significantly higher when LT-IIa, LT-IIb, or CT was co-administered with AgI/II. In addition, salivary IgA responses when T13 I mutant was co-administered with AgI/II were also significantly higher and comparable to the response with wt LT-IIa or LT-IIb. No significant response was observed with the T34 I mutant of LT-IIa up to Day 60. At later time points (>100 days), however, a detectible serum adjuvant response elicited by the T34 I mutant of LT-IIa was observed in the mice (FIG. 4).

Figure 2:
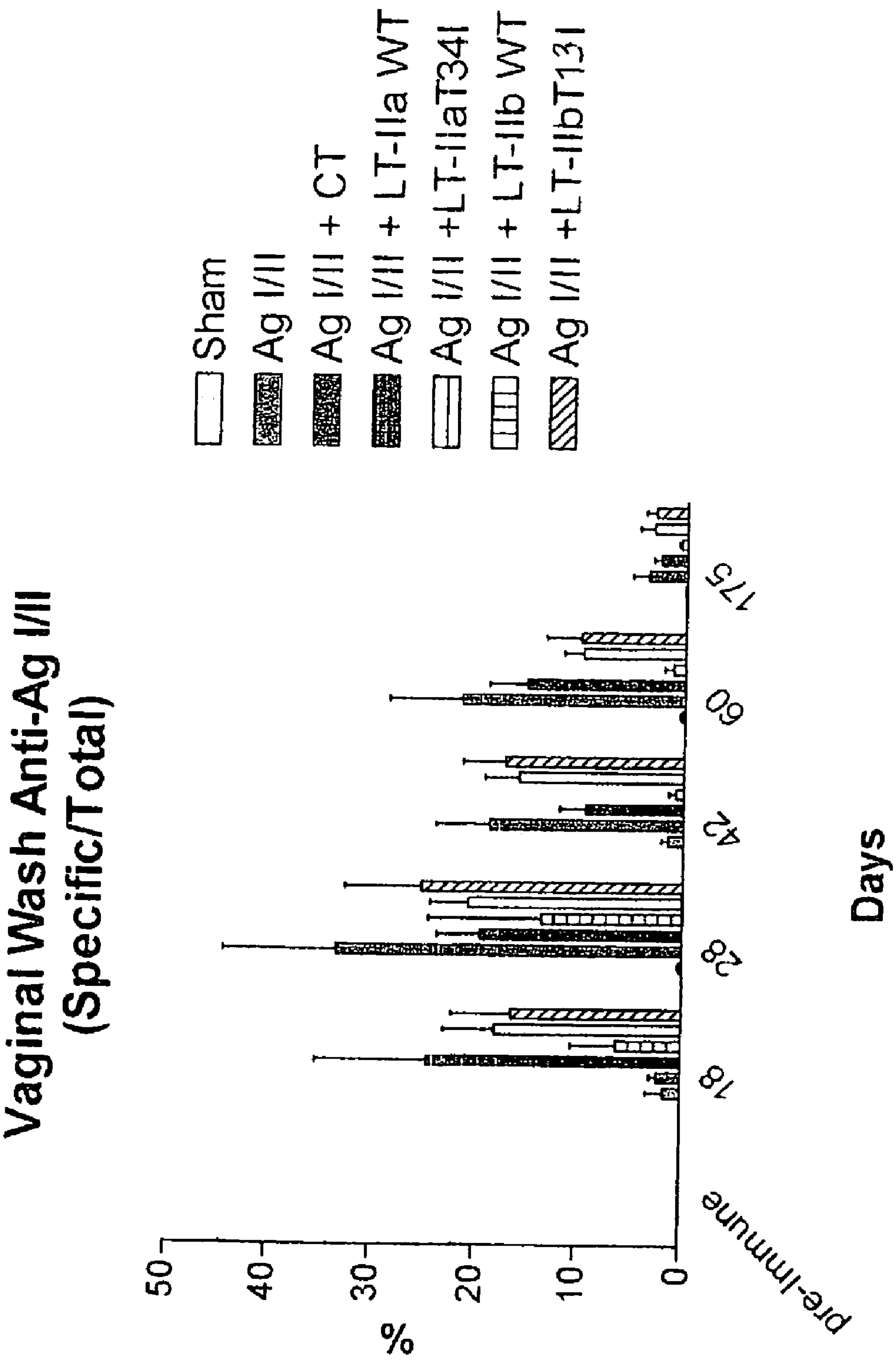
FIG. 2 is a representation of vaginal wash salivary IgA anti-Ag I/II levels with our without CT, wild type (WT) LT-IIa, LT-IIa—T34 I mutant, LT-IIb WT, and LT-IIb T-13I mutant. Data are shown at before immunization, and 18, 28, 42, 60 and 175 days after immunization.
Figure 3:
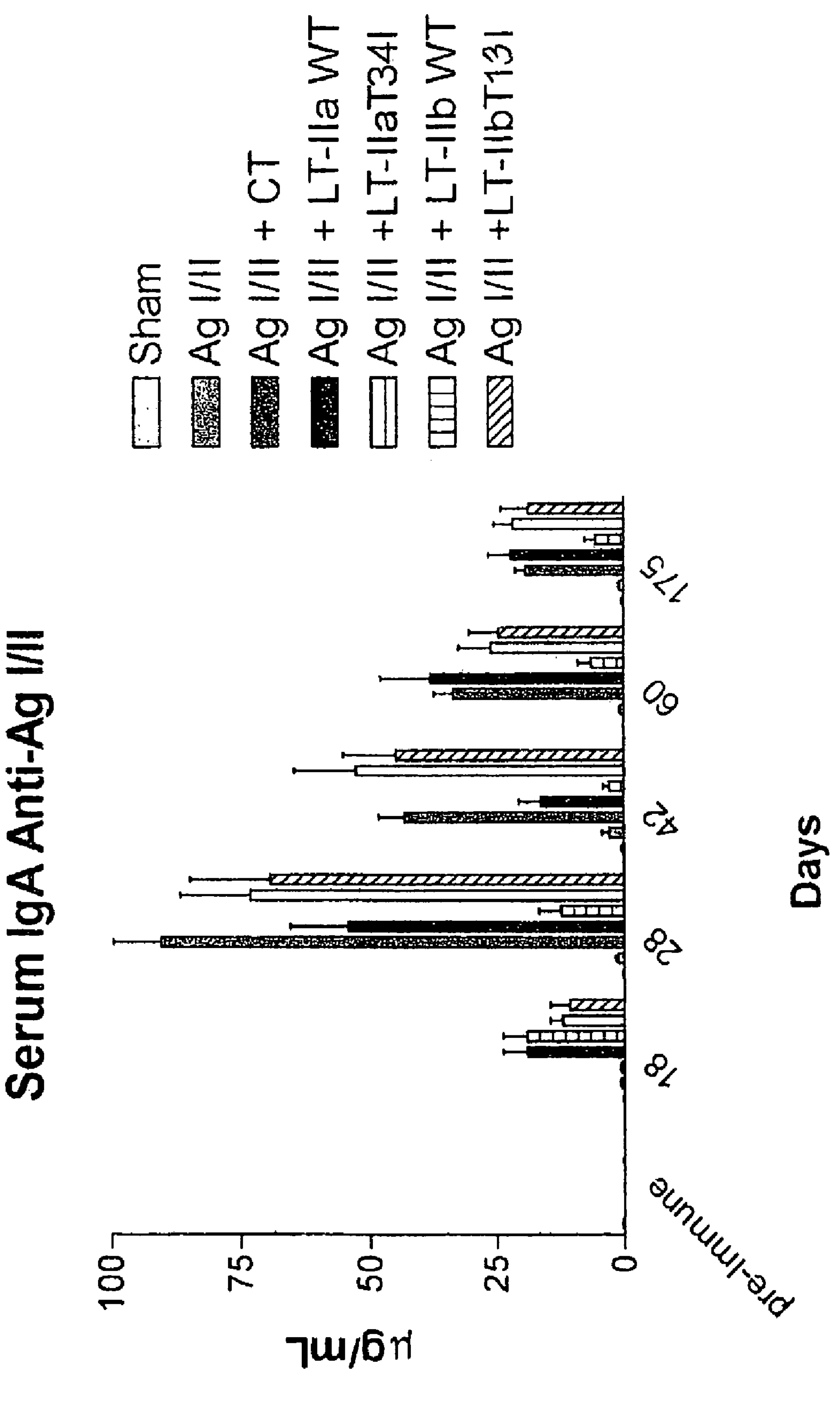
FIG. 3 is a representation of serum IgA anti-Ag I/II levels with our without CT, wild type (WT) LT-IIa, LT-IIa—T34 I mutant, LT-IIb WT, and LT-IIb T-131 mutant. Data are shown at before immunization, and 18, 28, 42, 60 and 175 days after immunization.

Similar results were also observed for vaginal IgA responses to AgI/II with or without CT, LT-IIa, LT-IIb or the mutants (FIG. 2). Immunoenhancing activity of the T131 mutant of LT-IIb was also observed in serum antibody responses to Ag/II. AgI/II-specific serum IgA and IgG were evaluated following administration as described above. For both IgG (FIG. 4) and IgA (FIG. 3), the response after 18 days, with the T13 I mutant was comparable to the immune response elicited by the LT-IIa and LT-IIb wild type mutants used as adjuvants while the response with the T34I mutant was significantly lower.

EXAMPLE 2

Figure 5:
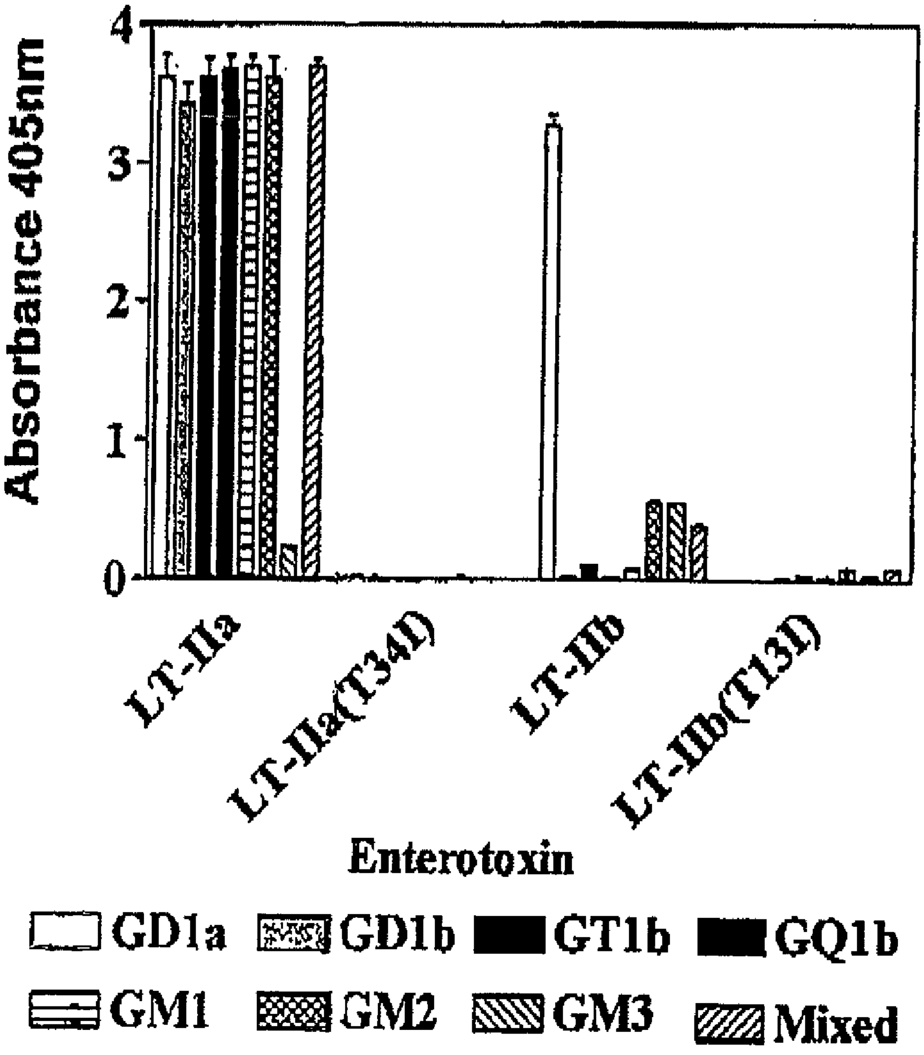
FIG. 5 is a representation of the ganlioside binding activity of wild type LT-IIa and LT-IIb and mutants thereof

This example demonstrates that the mutants of the present invention lack ganglioside binding activity. To confirm that the ganglioside-binding activities of the purified mutant enterotoxins were equivalent to those of the mutant enterotoxins in the crude extracts, binding of the purified wt and mutant enterotoxins for various gangliosides was measured by ganglioside-specific ELISA (Connell et al., 1992, Infect. Immun. 60:63-70; Connell et al., 1995, Mol. Microbiol. 16:21-31 (FIG. 5). While LT-IIa bound to gangliosides GD1b, GM1, GT1b, GQ1b, GD2, GD1a and GM3, LT-IIa(T34I) mutant, however, exhibited no detectible affinity for those gangliosides. Similarly, while LT-IIb bound strongly to GD1a and with lower affinity to GM2 and GM3, LT-IIb(T13I) mutant had no detectable binding affinity above background for GD1a, GM2, or GM3.

EXAMPLE 3

Figure 6:
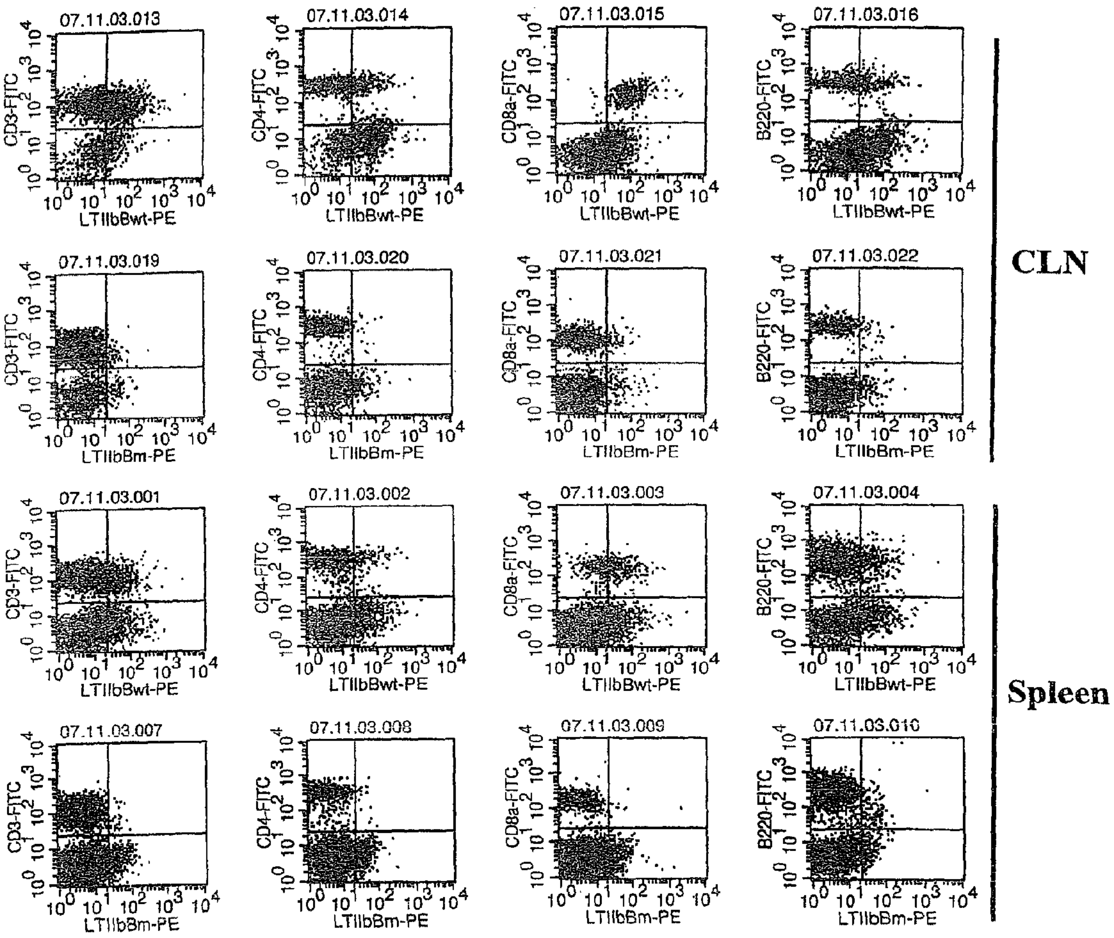
FIG. 6 is a representation of flow cytometric analysis of the binding activity of mutant and wild type LTIIb B pentamers for lymphoid cells of the B and T classes. Key: CLN is cervical lymph node cells; Spleen is splenic cells; LT-IInBwt-PE is wild type LT-IIb B pentamer labeled with PE; LT-IIbBm-PE is mutant LT-IIb B pentamer labeled with PE; CD3-FITC is cell surface marker for T-cells labeled with FITC; CD4-FITC is cell surface marker for CD4+ T cells labeled with FITC; CD8a-FITC is cell surface marker for CD8+ T cells labeled with FITC; and B220-FITC is cell surface marker for B cells labeled with FITC.

This example describes experiments to define the interactions between wt LT-IIa, wt LT-IIb, and the respective mutants of each, with lymphoid cells that control the adjuvant response. In this experiment, flow cytometric analysis (FACS) was performed to determine the binding activity of mutant and wild type LTIIb B pentamers for lymphoid cells of the B and T classes. Cells isolated from the cervical lymph node (CLN) and spleen of naive mice were initially stained with PE-labeled antibodies against mutant LTIIb B pentamer (LT-IIbBm-PE) or wild type (wt) LTIIb B pentamer (LT-IIbBwt-PE) and counterstained with one of the following FITC-labeled lymphoid cell surface marker-specific monoclonal antibody (mAb): B220+ (B cells), CD3 (T-cells), CD4 (CD4+ T cells), and CD8a (CD8+ T cells). As shown in FIG. 6, the wt LTIIbB bound CD3+ (T lymphocytes), CD4+ (CD4+ T cells), CD8+ (CD8+T cells) and B220+ (B lymphocytes) cells from both CLN and spleen. In contrast, mutant LTIIb exhibited little or no binding to B cells or to any T cell type isolated. A minor population of cells which was negative for all cell surface markers used in this study was bound by mutant LTIIbB. That cell population may be derived from a previously unidentified lymphoid lineage.

Figure 7:
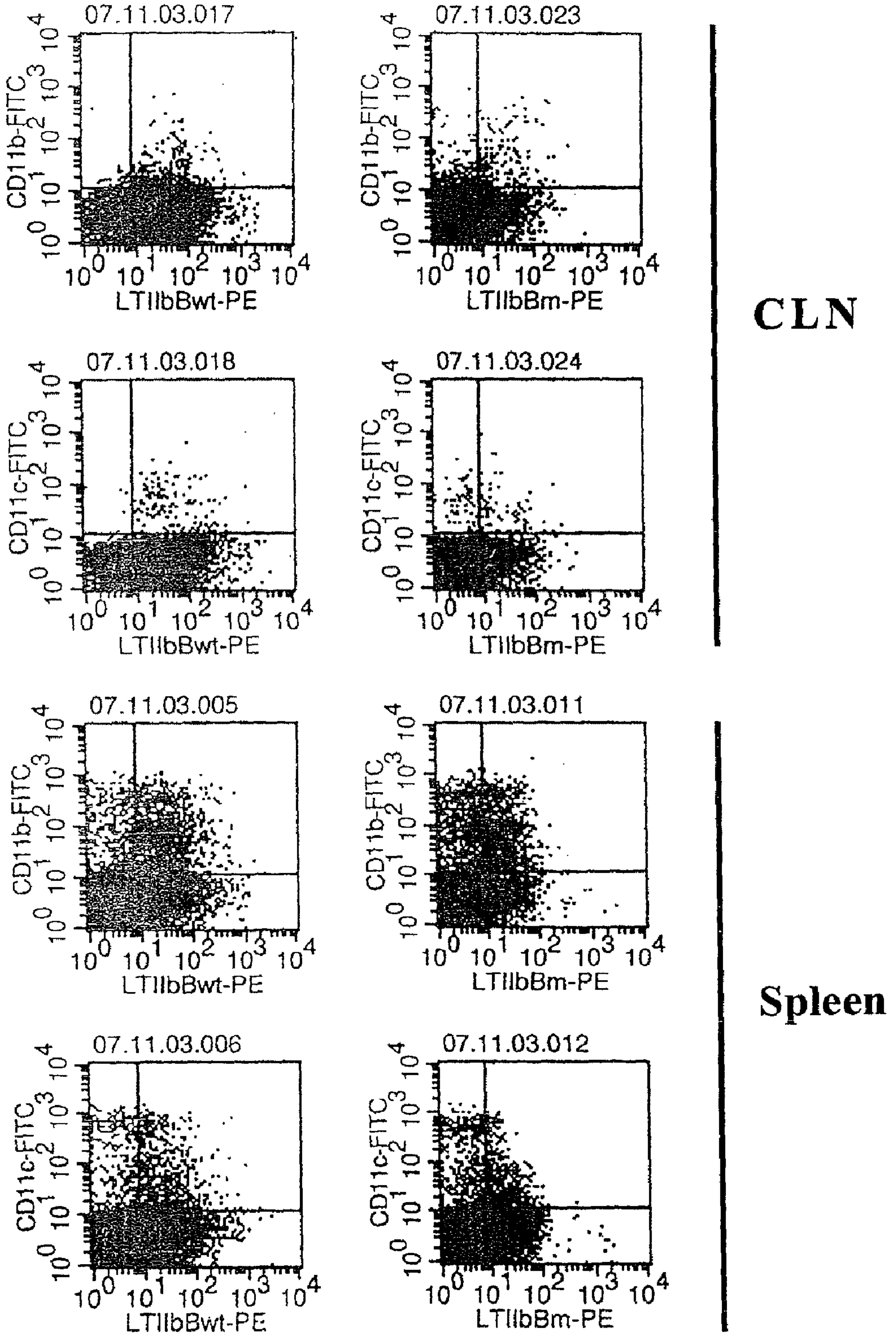
FIG. 7 is a representation of flow cytometric analysis of the binding activity of mutant LT-IIb B pentamer (LT-IIbBm-PE) and wt LT-IIb B pentamer (LT-IIbBwt-PE) on antigen presenting cells (macrophages and dendritic cells). Key: CLN is cervical lymph node cells; Spleen is splenic cells; LTIIbBwt-PE is wild type LT-IIb B pentamer labeled with PE; LT-IIbBm-PE is mutant LT-IIbB pentamer labeled with PE; CD11b-FITC is cell surface marker for macrophages labeled with FITC; and CD11c-FITC is cell surface marker for dendritic cells labeled with FITC.

A second flow cytometric analysis was performed to determine the binding activity of mutant LT-IIb B pentamer (LT-IIbBm-PE) and wt LT-IIb B pentamer (LT-IIbBwt-PE) on antigen presenting cells (macrophages and dendritic cells). Cells isolated from the CLN and spleen of naive mice were stained with PE-labeled antibodies against mutant LTIIb B pentamer or wild type LTIIb B pentamer and counterestained with FITC-labeled antibodies specific for CD11b and CD11c which recognized macrophages or dendritic cells, respectively. As shown in FIG. 7, wt LTIIbB binds to essentially all identifiable macrophage and dendritic cells; mutant LTIIbB has no binding activity for cells exhibiting CD11c (dendritic cells) and binds only weakly to CD11b cells (macrophages).

The results presented herein demonstrate that the mutant enterotoxins which lack ganglioside binding activity but retain adjuvant activity can be used for enhancing the immune response to antigens. Minor modifications to the embodiments described herein will be apparent to those skilled in the art and are intended to be within the scope of this invention.

The invention claimed is:

1. A method of enhancing an antibody immune response to an antigen comprising the steps of administering intranasally to an individual:

a) a mutant entertotoxin, wherein the mutant enterotoxin is a mutant of the B subunit of LT-IIb, wherein the mutant enterotoxin consists of the sequence of SEQ ID NO:6, and wherein the mutant enterotoxin, does not exhibit GD1a, GM2 and GM3 ganglioside binding activity, and b) the antigen, whereby the mutant enterotoxin acts as an adjuvant to enhance the antibody immune response to the antigen.

2. The method of claim 1, wherein the mutant enterotoxin and the antigen are administered simultaneously.

3. The method of claim 1, wherein the mutant enterotoxin and the antigen are administered sequentially.

4. The method of claim 1, wherein the individual is a human.

5. The method of claim 1, wherein the mutant enterotoxin and the antigen are administered as a fused molecule.

6. The method of claim 1, wherein the mutant enterotoxin and the antigen are administered as a chemically conjugated molecule.

7. The method of claim 1, wherein the mutant enterotoxin and the antigen are administered as a chimeric molecule.

8. The method of claim 1, wherein the antibody immune response to the antigen is an enhanced serum, salivary and vaginal antibody response.

* * * * *